United States Patent [19]
Augello et al.

[11] Patent Number: 6,099,865
[45] Date of Patent: Aug. 8, 2000

[54] CROSCARMELLOSE TASTE MASKING

[75] Inventors: Michael Augello, Marlboro, N.J.;
Sheila M. Dell, New Hope, Pa.;
George E. Reier, Somerset, N.J.;
Howard J. Stamato, Bridgewater, N.J.;
Lynn M. DiMemmo, Hamilton, N.J.

[73] Assignee: FMC Corporation, Philadelphia, Pa.

[21] Appl. No.: 09/330,445

[22] Filed: Jun. 11, 1999

Related U.S. Application Data

[60] Provisional application No. 60/091,996, Jul. 8, 1998.

[51] Int. Cl.$^7$ ...................................................... A61K 9/62
[52] U.S. Cl. ........................... 424/494; 424/489; 424/464; 424/495; 424/470
[58] Field of Search ..................................... 424/489, 464, 424/470, 468, 458

[56] References Cited

U.S. PATENT DOCUMENTS 5,874,418   2/1999   Stella et al. ................................ 514/58

FOREIGN PATENT DOCUMENTS 6091150   4/1994   Japan .

*Primary Examiner*—Thurman K. Page
*Assistant Examiner*—William E. Benston
*Attorney, Agent, or Firm*—FMC Corporation

[57] ABSTRACT

The present invention describes the use of croscarmellose sodium to coat bitter-tasting active agents in a manner that will mask the bitter taste of these materials, taste masked pharmaceutical compositions in which the particles of pharmaceutically active agent are coated with croscarmellose sodium, taste masked pharmaceutical tablets made therefrom, in which the rapid disintegration of tablets that is imparted by croscarmellose sodium is preserved, and to a method for preparing such coated particles by preparing them in a fluidized bed coating process.

12 Claims, No Drawings

CROSCARMELLOSE TASTE MASKING

This application claims benefit of Provisional Application Ser. No. 60/091,996 filed Jul. 8, 1998.

FIELD OF THE INVENTION

The present invention relates to the use of croscarmellose sodium to coat bitter-tasting active agents in a manner that will mask the bitter taste of these materials. More particularly the present invention relates to a particulate taste masked pharmaceutical composition in which particles of a pharmaceutically active agent are coated with croscarmellose sodium. It also relates to taste masked pharmaceutical tablets made therefrom, in which the rapid disintegration of tablets that is imparted by croscarmellose sodium is preserved. The invention also provides a method for preparing the particulate taste masked pharmaceutical compositions.

BACKGROUND OF THE INVENTION

Croscarmellose sodium has been widely used as a dispersant and disintegrant in the pharmaceutical industry. It is known to have been used as a "super disintegrant" for pharmaceutical tablets where rapid disintegration and/or dispersion is required to render pharmaceutical actives promptly physiologically available. Croscarmellose is typically used in such applications in combination with other pharmaceutically acceptable adjuvants such as binders, lubricants, dispersants, surface active agents and the like, all of which are well known to those skilled in the art of formulating pharmaceutically active agents.

Bitter tasting pharmaceutically active agents are particularly difficult to render palatable when placed in tableted dosage forms. Much research and many techniques have been employed in the art to effectively mask the taste of bitter tasting pharmaceuticals without retarding the physiological availability of the bitter tasting active ingredients. Well known methods for taste masking generally have involved coating of the particles of the active ingredient and/or the tablet containing such active ingredient, with various coating materials or combinations of coating materials many or most of which have limited water solubility and are therefore applied from organic media. However, on the one hand, the more water soluble such coatings are, the less effective they are in taste masking, and on the other hand the less water soluble they are the more they tend to retard the physiological availability of the active ingredient. Moreover, in order to achieve both rapid disintegration and taste masking it has been necessary to use both a coating and a disintegrant or super disintegrant, such as croscarmellose sodium, in the tablet formulation. This is extremely costly in requiring both a coating step and the addition of relatively costly disintegrants. Accordingly there is a continuing need for less costly and more effective methods for achieving taste masking while at the same time assuring prompt physiological availability of the active ingredient. It is a further advantage of the present invention that the coating solution employed herein is entirely aqueous, so that there is no organic residue left in the coated particles.

It has now been found that these and other objects of the invention can be achieved by utilizing croscarmellose sodium as both a coating agent and as a disintegrant, thereby eliminating the need for use of separate coating and disintegrants in tableting formulations. It has further been found that particle size of the active ingredient and the method used to coat the active both play an important role in the ability to use croscarmellose sodium to serve both functions. These findings are particularly surprising and unexpected in view of the fact that croscarmellose sodium has not heretofore been used as a taste masking agent.

BRIEF SUMMARY OF THE INVENTION

Accordingly, in accordance with a first aspect of this invention there is provided a particulate taste masked pharmaceutical composition comprising a substrate which consists essentially of particles of a pharmaceutically active agent having an objectionably bitter taste coated with a taste masking amount of croscarmellose sodium, the amount of the coating being in the range of 10 to 50 percent by weight of the substrate.

In accordance with a second aspect of this invention there is provided a method for masking the bitter taste of a pharmaceutically active agent without separate coating and disintegrant agents which comprises:

(a) fluidizing in fluidized bed coating apparatus a substrate having a particle size in the range of 50 to 500 microns consisting essentially of an objectionably bitter tasting pharmaceutically active agent;

(b) Spraying into said fluidized bed an aqueous solution of croscarmellose sodium an amount in the range of 10 to 50 percent by weight of said substrate; and (c) Recovering a taste masked coated pharmaceutical composition consisting essentially of said pharmaceutically active agent coated with a taste-masking amount of croscarmellose sodium.

In yet another embodiment of the invention there is provided a taste masked pharmaceutical dosage form comprising a tablet for oral administration consisting essentially of a therapeutically effective amount of the particulate composition of the coated active ingredient described above in admixture with one or more compatible pharmaceutically acceptable adjuvants, in which croscarmellose sodium serves as both taste masking agent and dispersant, without the need for additional dispersants or coating agents or steps.

DETAILED DESCRIPTION OF THE INVENTION

In accordance with the first aspect of this invention, the particulate taste masked pharmaceutical composition comprises particles of a pharmaceutically active agent having an objectionably bitter taste in which the particles of pharmaceutically active agent are coated with a taste masking amount of croscarmellose sodium. For purposes of this invention, in order to effectively taste mask the pharmaceutical composition described above, it is generally necessary to use slightly more croscarmellose sodium for purposes of taste masking than is normally employed when employing croscarmellose sodium as a super disintegrant for pharmaceutical tablets. In this invention, however, it is used to coat particles of the bitter tasting pharmaceutical active ingredient rather than as a simple additive or excipient which is blended with the active agent or ingredient and other adjuvants in the tableting formulation. As a coating material, it is employed in an amount in the range of 10 to 50 percent, preferably in the range of 15 to 28 percent, and most preferably from about 18 to about 25 percent by weight of the substrate to which it is applied as a taste masking coating. At these levels and when applied as a coating as described below, it serves the dual function of acting as a taste masking agent and as a super disintegrant for tableted dosage forms.

In addition to the use of appropriate amounts of croscarmellose sodium as a coating for the active ingredient, the particle size of the active ingredient is also important in achieving adequate taste masking. As shown in the examples below the taste masking efficacy of croscarmellose sodium is dramatically reduced when the particle size of the substrate is below about 60 microns and/or when a large percentage of the substrate has a fine particle size. Accordingly it is important to the present invention that the active ingredient which forms the substrate to be coated by the croscarmellose sodium have a particle size in the range of 50 to 500 microns, that not more than about 1 percent of the particles have a particle size smaller than 60 microns and/or that not more than about 1.5 percent of the substrate particles have a particle size less than about 125 microns. Accordingly it is preferred to use a substrate which is in crystalline form rather than in a powdered form. It is also important in the coating process to control the inlet temperature to maintain a temperature below the melting point of the substrate to be coated to that the substrate does not melt during the coating process.

In order to increase adherence croscarmellose to the active ingredient particles, a binder may be added to the coating solution or suspension. Suitable binders include ethylcellulose, hydroxypropylmethyl cellulose, methylcellulose, polyvinylpyrrolidone, or other binders conventionally employed in pharmaceutical preparations. In general these binders are used in the present invention at very low levels simply to assure that the croscarmellose coating strongly adheres to the particulate pharmaceutically active agent. Though these ranges may vary with the particular binder or formulation, they are suitably employed at levels in the range of about 4 up to about 10 percent by weight of the coated particulate product, including active ingredient and coating solids, but excluding water present in the coating solution, preferably in the range of about 4 to about 6 percent by weight. These levels are substantially below the level at which these binders are normally used for other purposes in some pharmaceutical preparations, for example as enteric coatings or taste masking agents.

Advantageously, plasticizers may also be included in the coating solutions or suspensions of the present invention for the purpose of plasticizing the ethylcellulose sufficiently to provide it with sufficient flexibility and hardness to prevent the coating from being abraded or destroyed when the coated particles are subsequently handled in processing equipment and/or compressed into tableted dosage forms. Suitable plasticizers include polyethylene glycol having a molecular weight in the range of 200 up to about 8000, propylene glycol, glycerin, glycerin triacetate, triethylcitrate, dibutylsebacate (DBS), or other conventional plasticizers for pharmaceutical preparations. The amount of plasticizer employed may vary over a wide range depending on the plasticizer used and the binder employed in the formulation, it is generally preferred to utilize sufficient plasticizer to provide from about 0.2 to about 3 percent by weight of the total particulate product.

In accordance with the process aspect of this invention, a fluidized bed coating apparatus is required to spray an aqueous solution or suspension of croscarmellose sodium, as described above, into a fluidized bed of the particulate pharmaceutical active substrate.

Fluidized bed coating machines are manufactured by numerous companies. One, a Wurster coater, is essentially a bowl in which the substrate to be coated is placed and air is blown from the bottom to create the fluid condition of the solid. In the Wurster coater, a spray nozzle is placed under the fluidized bed, providing a bottom spray which coats the fluidized particles. A preferred method of coating the particles utilizes a fluidized bed which operates similarly to the Wurster apparatus, but has a spray nozzle located above the fluidized bed, providing a downwardly directed spray which coats the particles. One manufacturer of a top spray fluidized bed coater is the Niro Company. The top spray appears to provide a better coating and actually increases the average particle size of the coated particles of active agent. A common characteristic of all fluidized bed coating operations is that these are batch operations.

Thus the preferred process aspect of this invention is a coating process in which a granular substrate is directly coated. Although wet granulation techniques have been attempted in an effort to increase particle size of the active ingredients with and without croscarmellose sodium prior to fluidized bed coating with croscarmellose sodium, these techniques were not found to be as effective to achieve taste masking as simply coating the crystalline materials and involved extra processing steps rendering them less cost effective. Thus, while such additional steps are contemplated as within the scope of this invention, they are not considered the best mode for practicing the invention.

The substrate can be any solid, preferably crystalline, pharmaceutical active ingredient which has a bitter taste that requires taste masking. Examples of suitable substrates include acetaminophen, ibuprofen, ketoprofen, other similar members of this class of nonsteroidal anti-inflammatory agents, guiafenesin, dextromethorphan, chloropheniramine, and bromopheniramine. The active ingredient may be highly water soluble or have limited water solubility. Those skilled in the art of taste masking will appreciate that numerous other pharmaceutical actives which have a particularly objectionable bitter taste may also be taste masked in accordance with the present invention.

It will be appreciated by those skilled in the coating and/or taste masking art that some experimentation may be required with each machine and/or active ingredient, to ascertain the optimum particle size distribution of coated particulate pharmaceutically active material. It will also be appreciated that once this has been ascertained for a particular coating machine and/or pharmaceutical active, the product could be screened to remove particles smaller than a particular dimension, without departing from the spirit and scope of this invention. This material passing through an appropriately sized screen could be utilized in applications where taste masking of the active is not required, and thus make the process even more cost effective.

When the coated substrate is incorporated into the final tablet formulation, the amount of croscarmellose sodium in the tableted formulation will generally be in the range of about 1–10% by weight of the finished tablets. Since this is at or slightly above the range at which croscarmellose sodium is normally employed as a disintegrant in tablets or tableting formulations its dual functionality as a coating and taste masking agent and as a disintegrant for tablets formed from the coated composition of this invention will be readily apparent to those skilled in the formulation and taste masking art.

The product of the process is preferably a free flowing particulate granular material comprising the particulate pharmaceutically active agent having a coating comprising croscarmellose sodium, a binder, and optionally a plasticizer. The product may be compressed as such into taste-masked tableted dosage forms, or may be blended with tableting additives conventionally used in the formulation of pharmaceutical tablets then compressed into a tableted dosage forms. Such additives include, for example, fillers such as microcrystalline cellulose and/or various gums, sweeteners such as Aspartame®, Prosweet®, mannitol, sucrose, or other sweetners, flow aids such as magnesium stearate, and other additives conventionally employed in preparing tableting formulations.

The following examples further illustrate the practice of the present invention. These examples are for illustration purposes only and are not intended to limit the scope of the invention except as described elsewhere in the specification or claims. In the accompanying examples all percentages are percent by weight unless otherwise indicated. In each of the examples the percentage of taste masking was determined by submitting a sample to 15 to 20 people who tasted the sample and compared it with a control sample and reported whether on not in their opinion the test sample effectively masked the bitter taste of the active ingredient. The percentage number given in the example is thus a reflection of the percentage of tests in which the test sample was judged effectively taste masked.

Example 1 describes the preferred method of coating crystalline acetaminophen with a croscarmellose solution using a top spray and a fluidized bed. Example 2 shows the preparation of tablets and results of the taste masking produced by the coatings of Example 1 and relates the effectiveness to particle sizes shown in Example 1. Example 3, shows the effectiveness of taste masking in which the total coated material is utilized and compared with a fraction of the particles of the same material larger than 149 microns. Also, there is the comparison with a commercial, solvent-coated acetaminophen. Example 4 is indicative of the lower limit of croscarmellose sodium which must be used to provide effective taste masking. Example 5 is a comparative example to show the effect of no coating at all. Example 6 uses the same commercial, solvent-coated, crystalline acetaminophen that was used in Example 3, and is included to show the greatly reduced friability of using croscarmellose sodium-coated acetaminophen in a rapid tablet press as compared with the current commercial material. Examples 7 and following demonstrate the coating process of the present invention with ibuprofen, guiafenesin and acetaminophen utilizing a binder and plasticizer in the coating solution.

EXAMPLE 1

In a fluidized bed coater with a bowl insert was placed 1.0 Kg of crystalline acetaminophen. A slurry of 250 grams of croscarmellose in 3322 grams of water, a 7% solids slurry, was prepared. This slurry was top-sprayed onto the fluidized bed of acetaminophen, requiring approximately 2 hours to complete the coating process. During the coating process the inlet temperature and the outlet temperature were maintained at 80° C. and 36° C., respectively. The percentages of particles of various sizes were determined by passing the product through a stack of sieves, each one finer than the one above it. This is Example 1A for which the particle size distribution is shown in Table 1. Two additional identical coatings were made except that double the amount of each material was used. These are Examples 1B and 1C. Sieve analysis data for each of these materials are shown in Table 1 also. A comparative sieve analysis of the substrate crystalline acetaminophen is also included in Table 1.

TABLE 1

| Particle size | Crystalline | Example | | |
|---|---|---|---|---|
| (microns) | APAP | 1A | 1B | 1C |
| >500 | 0.53% | 9.17% | 10.21% | 3.57% |
| 297–500 | 66.44% | 87.13% | 86.96% | 73.90% |
| 210–297 | 32.59% | 2.68% | 1.31% | 9.13% |
| 125–210 | 0.44% | 0.46% | 0.19% | 3.77% |
| 62–125 | 0 | 0.56% | 0.28% | 4.07% |
| <62 | 0 | 0 | 1.05% | 5.56% |

EXAMPLE 2

In a large twin shell blender were placed 253.2 grams of acetaminophen crystals which had been sprayed with a slurry of croscarmellose sodium (Example 1A) and 189.9 grams of Avicel® CE-15 (microcrystalline cellulose/guar gum, 85/15, sold by FMC Corporation, Philadelphia, Pa. 19103). These components were blended for 10 minutes. At the end of this period, 113.9 grams of Avicel PH-102, 25.3 grams of Aspartame® powder, and 25.3 grams of ProSweet® were added to the blender, and mixing was continued for an additional 10 minutes. Next, 384.9 grams of granular mannitol was added to the blender, followed by 10 more minutes of mixing. Finally, 7.6 grams of magnesium stearate which had been passed through a 30 mesh US Standard screen was added and blended for 3 minutes. This composition was compressed on a $B_2$ tablet press operated at 39 RPM and fitted with round, 9.525 mm (0.375 inch) diameter, standard convex tooling. The upper compression force was in the range of 900 to 1100 Kg and the lower compression force averaged 1000 Kg. The average weight, thickness, and hardness of these tablets were, respectively, 0.413 gram, 5.56 mm (0.2189 inch), and 7.64 Kp. Friability after 4 minutes was 0.0239%, and tablet disintegration time in 37° C. water without stirring was approximately 2 minutes. Taste masking was approximately 95%. This is Example 2A. Two additional identical formulations, Examples 2B and 2C, were prepared, respectively, from acetaminophen coated with croscarmellose sodium in Examples 1B and 1C. Formulation 2B was taste masked less than Formulation 2A and exhibited some of the characteristic bitterness of acetaminophen. Formulation 2C was taste masked to a lesser degree than either Formulation 2A and exhibited minor bitterness of the acetaminophen. The tablet properties of these tablets are shown in Table 2.

TABLE 2

| | Example | | |
|---|---|---|---|
| Tablet Property | 2A | 2B | 2C |
| Weight (gram) | 0.413 | 0.384 | 0.3721 |
| Thickness (mm) | 5.56 | 4.37 | 4.33 |
| Hardness (Kp) | 7.64 | 5.94 | 4.37 |
| Compression force | | | |
| Upper (Kg) | 900–1100 | NR[a] | NR |
| Lower (Kg) | 1000 | NR | NR |
| Disintegration (min) | ~2 | <1 | <1 |
| Friability (%) | 0.0239% | 0.125% | 0.252% |

[a]NR- not recorded

EXAMPLE 3

Using the procedure of Example 2, 25.27 grams of acetaminophen powder which had been coated with a slurry of croscarmellose sodium in a Wurster fluidized bed using a bottom spray was placed in a twin shell blender. The weight ratio of acetaminophen powder to croscarmellose sodium was 85:15. Then, 16.13 grams of Avicel® CE-15 (microcrystalline cellulose/guar gum, 85/15, sold by FMC Corporation, Philadelphia, Pa. 19103) was added to the blender and blended for 10 minutes. At the end of this period, 5.10 grams of Avicel PH-102, 4.84 grams of Aspartame® powder, 0.54 gram of Enhance® and 1.07 grams of ProSweet® were added to the blender, and mixing was continued for an additional 10 minutes. Next, 46.24 grams of granular mannitol was added to blender, followed by 10 more minutes of mixing. Finally, 0.8 gram of magnesium stearate which had been passed through a 30 mesh US Standard screen was added and blended for 3 minutes. This composition was compressed on an F tablet press fitted with round, 9.525 mm (0.375 inch) diameter, standard convex tooling. The average weight, thickness, and hardness of these tablets were, respectively, 0.3496 gram, 4.44 mm (0.1749 inch), and 3.44 Kp. Friability after 4 minutes was 1.0%, and tablet disintegration time in 37° C. water without stirring was less than 30 seconds. Taste masking was approximately 85%. This is Example 3A.

A portion of the coated acetaminophen powder used to prepare Example 3A was passed through a 100 mesh U.S. Standard screen, and the portion remaining on the screen, i.e., the particles that were larger than 149 microns, was used in an identical formulation to Example 3A to prepare the tablets of Example 3B. Taste masking was improved to 90% by using only the larger coated particles.

A comparative formulation was prepared in which commercial coated, crystalline acetaminophen (Eurand America) replaced the croscarmellose-coated acetaminophen. The Eurand material is a solvent-coated material, making slight adjustments necessary in the weights of other components to provide the same amount of acetaminophen per tablet. This comparative formulation is Example 3C which provided 95% taste masking of the acetaminophen. The formulations of Examples 3A, 3B, and 3C are shown in Table 3, and the corresponding tablet properties are shown in Table 4.

TABLE 3

| Formulation Components | Example 3A (grams) | 3B (grams) | 3C (grams) |
| --- | --- | --- | --- |
| Coated APAP | 25.27[a] | 25.27[b] | 24.25[c] |
| Avicel PH-102 | 5.10 | 5.10 | 5.18 |
| Mannitol[d] | 46.24 | 46.24 | 46.87 |
| Avicel CE-15 | 16.13 | 16.13 | 16.35 |
| Aspartame | 4.84 | 4.84 | 4.90 |
| Pro Sweet | 1.07 | 1.07 | 1.09 |
| Enhance | 0.54 | 0.54 | 0.54 |
| Mg stearate | 0.82 | 0.82 | 0.82 |

[a]Croscarmellose sodium-coated acetaminophen powder comprising particles larger and smaller than 149 microns
[b]Croscarmellose sodium-coated acetaminophen powder in which all particles were larger than 149 microns
[c]Coated acetaminophen (Eurand America)
[d]Granular mannitol

TABLE 4

| Tablet Property | Example 3A | 3B | 3C |
| --- | --- | --- | --- |
| Weight (gram) | 0.3496 | 0.3614 | 0.416 |
| Thickness (mm) | 4.44 | 4.45 | 4.62 |
| Hardness (Kp) | 3.44 | 4.67 | 9.1 |
| Disintegration (min) | <0.5 | <0.5 | <3 |
| Friability (%) | 1.0 | 0.83 | 0.65 |

EXAMPLE 4

In a large twin shell blender were placed 228.5 grams of acetaminophen powder which had been coated with a slurry of croscarmellose sodium in a Wurster fluidized bed apparatus using a bottom spray. The ratio of acetaminophen to croscarmellose sodium was 94:6. Also added to the blender were 107.5 grams of Avicel® CE-15 (microcrystalline cellulose/guar gum, 85/15, sold by FMC Corporation, Philadelphia, Pa. 19103), 32.2 grams of Aspartame® powder, 26.9 grams of ProSweet®, 21.5 grams of fruit punch flavor, and 2.69 grams of anhydrous citric acid. These components were blended for 10 minutes. At the end of this period, 53.8 grams of Avicel PH-102 and 518 grams of granular mannitol were added to the blender, and mixing was continued for an additional 5 minutes. Finally, 8.0 grams of magnesium stearate which had been passed through a 30 mesh US Standard screen was added and blended for 5 minutes. This composition was compressed on a 512 tablet press fitted with round, 9.525 mm (0.375 inch) diameter, standard convex tooling. There was very slight taste masking exhibited by these tablets.

EXAMPLE 5

In a twin shell blender were placed 64.35 grams of acetaminophen crystals and 60.33 grams of Avicel® CE-15 (microcrystalline cellulose/guar gum, 85/15, sold by FMC Corporation, Philadelphia, Pa. 19103). These components were blended for 10 minutes. At the end of this period, 36.48 grams of Avicel PH-102, 6.04 grams of Aspartame® powder, and 6.04 grams of ProSweet® were added to the blender, and mixing was continued for an additional 10 minutes. Next, 120.83 grams of granular mannitol was added to blender, followed by 10 more minutes of mixing. Finally, 2.4 grams of magnesium stearate which had been passed through a 30 mesh US Standard screen was added and blended for 3 minutes. This composition was compressed on a $B_2$ tablet press operated at 39 RPM and fitted with round, 9.525 mm (0.375 inch) diameter, standard convex tooling. The upper compression force averaged 1900.5 Kg. The average thickness and hardness of these tablets were, respectively, 4.32 mm (0.1699 inch), and 5.38 Kp. Tablet disintegration time in 37° C. water without stirring was less than 1 minute. There was no taste masking, and the tablets were described as having a bitter, metallic taste with a long-lasting aftertaste.

EXAMPLE 6

In a large twin shell blender were placed 253.2 grams of solvent-coated commercial acetaminophen (Eurand America) and 189.9 grams of Avicel® CE-15 (microcrystalline cellulose/guar gum, 85/15, sold by FMC Corporation, Philadelphia, Pa. 19103). These components were blended for 10 minutes. At the end of this period, 113.9 grams of Avicel PH-102, 25.3 grams of Aspartame® powder, and 25.3 grams of ProSweet® were added to the blender, and mixing was continued for an additional 10 minutes. Next, 384.8 grams of granular mannitol was added to blender, followed by 10 more minutes of mixing. Finally, 7.6 grams of magnesium stearate which had been passed through a 30 mesh US Standard screen was added and blended for 3 minutes. This composition was compressed on a $B_2$ tablet press operated at 39 RPM and fitted with round, 9.525 mm (0.375 inch) diameter, standard convex tooling. The average weight, thickness, and hardness of these tablets were, respectively, 0.3921 gram, 4.39 mm (0.173 inch), and 6.53 Kp. The friability of these tablets was 2.84%, and the disintegration time in 37° C. water without stirring was less than 1 minute. An upper compression force of at least 1500 Kg was required to provide tablets having the properties described above. There was, however, approximately 95% taste masking of the bitter taste of acetaminophen.

EXAMPLE 7

A large beaker was charged with 2464.5 grams of deionized water which was stirred with a propeller stirrer. To this water was added 185.5 grams of croscarmellose sodium. Mixing was continued for one hour to fully hydrate the croscarmellose sodium. In a second container, 193 grams of 30% ethylcellulose solution (Aquacoat® ECD, FMC Corporation) and 14.8 grams of polyethylene glycol 8000 (Union Carbide Corporation) were stirred for one hour to fully hydrate the polyethylene glycol. The two solutions were mixed and stirred for an additional 0.5 hour. The solution was then top sprayed using a Niro MP-1 fluidized bed on 741.8 grams of ibuprofen powder. The inlet temperature was 69–73° C. and the outlet temperature 33–38° C. The velocity of the air passing through the fluidized bed ranged from 42–74 cubic meters per hour, and the temperature of the ibuprofen ranged from 36–48° C. Spraying required a total of 2.5 hours. This Example 7A.

By the same method as Example 7A, 600 grams of ibuprofen was coated with a combination of 250 grams of croscarmellose sodium, 20 grams of polyethylene glycol, and 435 grams of 30% ethylcellulose solution in 3322 grams of deionized water. The following ranges of conditions were recorded: inlet temperature 62–73° C., outlet temperature 33–37° C., air velocity 41–79 cubic meters per hour, and the ibuprofen temperature 35–48° C. Spraying required about four hours. This is Example 7B.

EXAMPLE 8

By the method of Example 2, a dry blend comprising 164.7 grams of ibuprofen coated with the slurry of croscarmellose sodium, ethylcellulose, and polyethylene glycol (Example 7B), 79.0 grams of Avicel® PH-102, 592.4 grams of granular mannitol, 99 grams of Avicel® CE-15, 19.7 grams of aspartame was tableted with sweeteners and flavorings to provide taste masked Ibuprofen tablets.

EXAMPLE 9

By the method of Example 7, 740 grams of powdered guiafenesin was coated with 187.3 grams of croscarmellose sodium, 14.8 grams of polyethylene glycol 8000, and 193 grams of a 30% solution of ethylcellulose in 2488 grams of deionized water. The following ranges of conditions were recorded: inlet temperature of the fluidized bed 75–76° C., outlet temperature 35–39° C., temperature of the guiafenesin 37–43° C., and velocity of the air 26–60 cubic meters per hour. Spraying required nearly four hours. This is Example 9A.

By the same method, 600 grams of guiafenesin was coated with 250 grams of croscarmellose sodium, 20 grams of polyethylene glycol 8000, and 434 grams of a 30% ethylcellulose solution in 3322 grams of deionized water. The following ranges of conditions were recorded: inlet temperate 74–82° C., outlet temperature 35–41° C., temperature of the guiafenesin 37–52° C., and air flow velocity 22–51 cubic meters per hour. Spraying required about 5.7 hours. This is Example 9B.

EXAMPLE 10

By the method of Example 2, a dry blend comprised of 164.7 grams of guiafenesin coated with the slurry of croscarmellose sodium, ethylcellulose, and polyethylene glycol (Example 7B), 79.0 grams of Avicel® PH-102, 592.4 grams of granular mannitol, 99 grams of Avicel® CE-15, 19.7 grams of Aspartame® was tableted with sweeteners and flavorings to provide a taste masked guiafenesin tablet.

EXAMPLE 11

In a large stainless steel vessel was placed 124.3 Kg of purified water. The water was stirred with a propeller-type mixer, and 11.1 Kg of croscarmellose was added to the vortex of the stirred water. This mixture was stirred for 30 minutes. Simultaneously, in a second stainless steel container was placed 11.7 Kg of a 30% ethylcellulose aqueous dispersion. This dispersion was stirred with a propeller-type mixer, and 0.9 Kg of polyethylene glycol 8000 was added to the vortex of the dispersion. This mixture was stirred for 30 minutes. The ethylcellulose/polyethylene glycol dispersion was then added to the dispersion of croscarmellose sodium, and the combination was stirred for an additional 30 minutes. A total of 29 Kg of purified water was added to reduce the solids content of the dispersion to about 7%. A Glatt GPCG 60 fluidized bed system fitted 3–6 head spraying system in the top spray mode was charged with 44.5 Kg of granular acetaminophen. The inlet air temperature was in the range of 60–100° C. and the exhaust air temperature was maintained between 35° C. and 50° C. The spray rate was 100–300 grams of dispersion per minute per spray head. Spraying was completed in about 3.25 hours, yielding 59.03 Kg of coated acetaminophen. Dissolution of these granules in USP Apparatus 2 (paddle). 50 rpm, 900 mL of 0.05 M phosphate buffer, ph 5.8 showed that 104±9.9% of the acetaminophen was released in 10 minutes.

We claim:

1. A taste masked pharmaceutical composition comprising a substrate which consists essentially of particles of a pharmaceutically active agent having an objectionably bitter taste coated with croscarmellose sodium in an amount in the range of 10 to 50 percent by weight of the substrate.

2. The composition of claim 1 in which the substrate has a particle size in the range of 50 to 500 microns, not more than about 1 percent of which have a particle size smaller than 60 microns.

3. The composition of claim 2 in which not more than about 1.5 percent of the substrate particles have a particle size less than 125 microns.

4. The composition of claim 1 the substrate is coated with croscarmellose sodium, a binder and a plasticizer.

5. The composition of claim 4 in which said binder is ethylcellulose which comprises from 4 to 10 percent by weight of the taste masked pharmaceutical compositions and the plasticizer is polyethylene glycol.

6. The composition of claim 1, in which the substrate is coated with croscarmellose sodium by spraying an aqueous solution of croscarmellose sodium into a fluidized bed of said substrate.

7. The composition of claim 4 in which the croscarmellose sodium solution also includes a binder, a plasticizer or both of them.

8. The composition of claim 5 in which the binder is ethylcellulose and the plasticizer is polyethylene glycol.

9. A method for masking the bitter taste of a pharmaceutically active agent which comprises
   (a) fluidizing in fluidized bed coating apparatus a substrate having a particle size in the range of 50 to 500 microns consisting essentially of an objectionably bitter tasting pharmaceutically active agent;
   (b) Spraying into said fluidized bed an aqueous solution of croscarmellose sodium an amount in the range of 10 to 50 percent by weight of said substrate; and
   (c) Recovering a taste masked coated pharmaceutical composition consisting essentially of said pharmaceutically active agent coated with a taste-masking amount of croscarmellose sodium.

10. The method of claim 9 in which the substrate has a particle size in the range of 50 to 500 in which not more than about 1 percent of which have a particle size smaller than 60 microns.

11. The method of claim 10 in which not more than about 1.5 percent of the substrate particles have a particle size less than 125 microns.

12. A taste masked pharmaceutical dosage form comprising a tablet for oral administration consisting essentially of a therapeutically effective amount of the composition of claim 1 in admixture with one or more compatible pharmaceutically acceptable adjuvants.

* * * * *